US00PP24651P3

(12) United States Plant Patent
Craigie et al.

(10) Patent No.: US PP24,651 P3
(45) Date of Patent: Jul. 15, 2014

(54) ***AGAPANTHUS ORIENTALIS* PLANT NAMED 'PMN06'**

(50) Latin Name: *Agapanthus orientalis*
Varietal Denomination: PMN06

(76) Inventors: John Maxwell Craigie, Pine Mountain (AU); Gail Alexis Craigie, Pine Mountain (AU)

( * ) Notice: Subject to any disclaimer, the term of this patent is extended or adjusted under 35 U.S.C. 154(b) by 0 days.

(21) Appl. No.: 11/903,036

(22) Filed: Sep. 20, 2007

(65) Prior Publication Data

US 2010/0050307 P1 Feb. 25, 2010

Related U.S. Application Data

(60) Provisional application No. 60/846,050, filed on Sep. 20, 2006.

(51) Int. Cl.
*A01H 5/00* (2006.01)

(52) U.S. Cl.
USPC ..... Plt./398

(58) Field of Classification Search
USPC ..... Plt./398
See application file for complete search history.

(56) References Cited

PUBLICATIONS

Plant Variety Journal Quarter 4 vol. 18 No. 4 Mar. 1, 2006. p. 1 and 21.*

* cited by examiner

*Primary Examiner* — Annette Para
(74) *Attorney, Agent, or Firm* — Samuel R McCoy, Jr.

(57) ABSTRACT

'PMN06' is a distinctive variety of *Agapanthus orientalis*, which is characterized by its distinctive violet-blue and white bicolored flowers. These are expressed as a white inner perianth tube color and perianth lobes in contrast to a violet blue outer perianth tube color. These violet-blue and white bicolored flowers are borne on stems up to 90 cm high typically developing in late spring and early summer.

5 Drawing Sheets

Latin name of the genus and species: The Latin name of the novel variety disclosed herein is *Agapanthus orientalis* 'PMN06'.

Variety denomination: The inventive variety of *Agapanthus orientalis* disclosed herein has been given the variety denomination 'PMN06'.

BACKGROUND OF THE INVENTION

The present invention relates to a new and distinct variety of evergreen perennial *Agapanthus orientalis*, which has been named 'PMN06'. *Agapanthus* is a genus of ornamental plants which are native to South Africa. The new variety *Agapanthus orientalis* 'PMN06' is the result of a breeding program aimed at producing an *Agapanthus orientalis* variety with distinctive blue and white bicolored flowers. Violet-blue and white bicolored flowers on stems up to 90 cm high typically develop in late spring and early summer.

An application for Plant Breeders Rights for 'PMN06' has been lodged with the Australian Plant Breeders Rights Office, and was accepted on 4 Nov. 2005 (under Application No. 2005/318).

Parentage: The cultivar 'PMN06' was the result of a controlled pollination in 1999 at Pine Mountain, Queensland, Australia, in which the parent variety, breeder's code 'PMN01' (unpatented) was selfed to breeder's code 'PMN01' (unpatented). The parent form is characterized by a tall plant height, wide leaf width, erect leaf attitude, and weak violet blue and white bicolored flowers. Selection criteria for 'PMN06' were bicolored flowers, large inflorescence size and a high density of flowers in the inflorescence.

Asexual reproduction. The new variety 'PMN06' was first asexually propagated by vegetative division in the state of Queensland, Australia in 2002 and has been asexually propagated since that time by division and micropropagation. The distinctive characteristics of cultivar 'PMN06' have remained stable and true to type through successive cycles of asexual propagation.

SUMMARY OF THE INVENTION

'PMN06' is a distinctive variety of *Agapanthus orientalis*, which is characterized by its distinctive violet-blue and white bicolored flowers. These are expressed as a white inner perianth tube color and perianth lobes in contrast to a violet blue outer perianth tube color.

Violet-blue and white bicolored flowers on stems up to 90 cm high typically develop in late spring and early summer.

DETAILED BOTANICAL DESCRIPTION OF THE VARIETY

Figure 1:
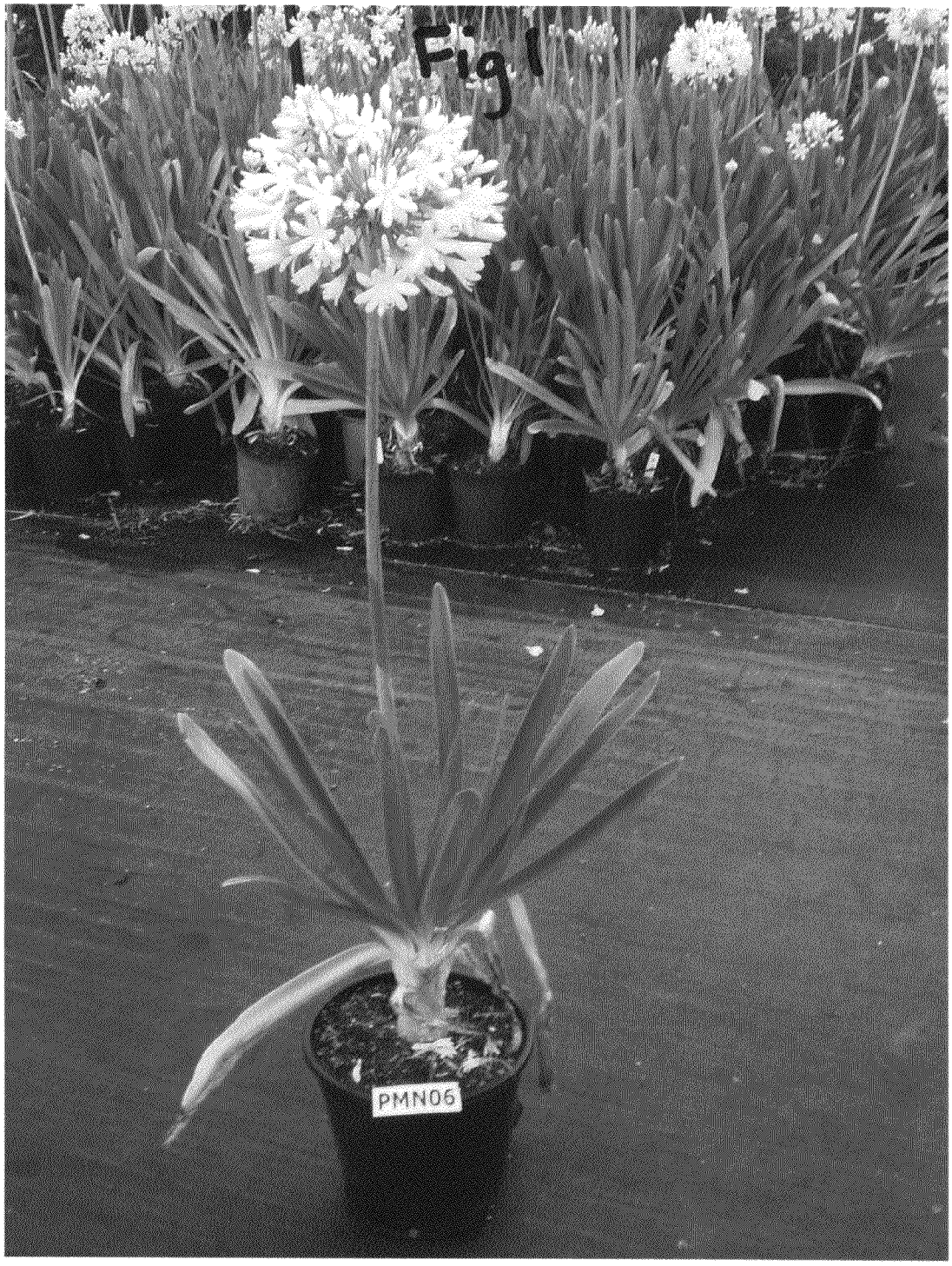
FIG. 1 shows an exemplary *Agapanthus orientalis* 'PMN06' plant at approximately 10-months of age from division of a mature clump. The plant was propagated and was transferred to a 250 mm diameter pot size and grown out in full sun.
Figure 2:
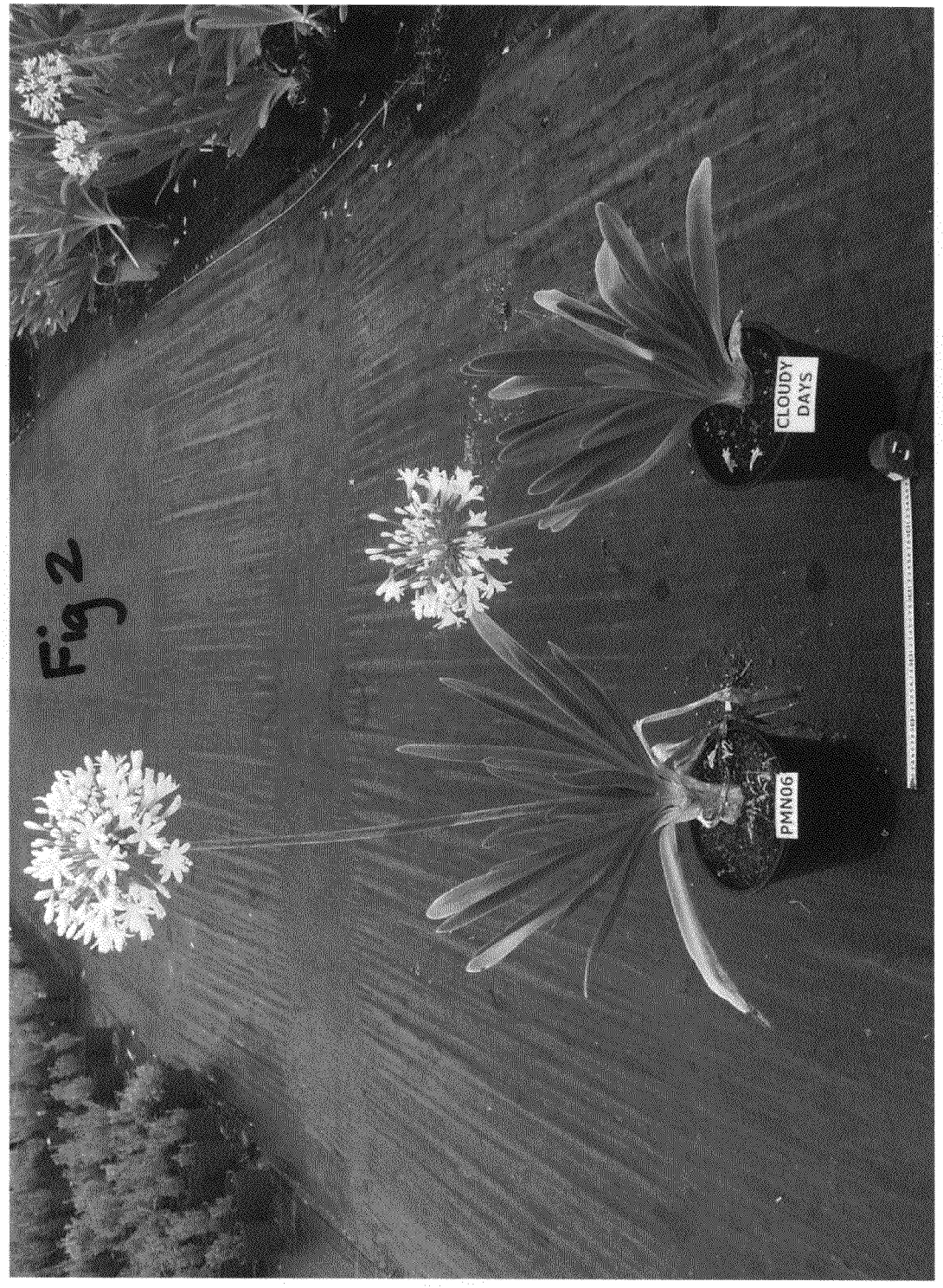
FIG. 2 shows a comparison between 'PMN06' (on left) and the similar variety 'Cloudy Days'.
Figure 3:
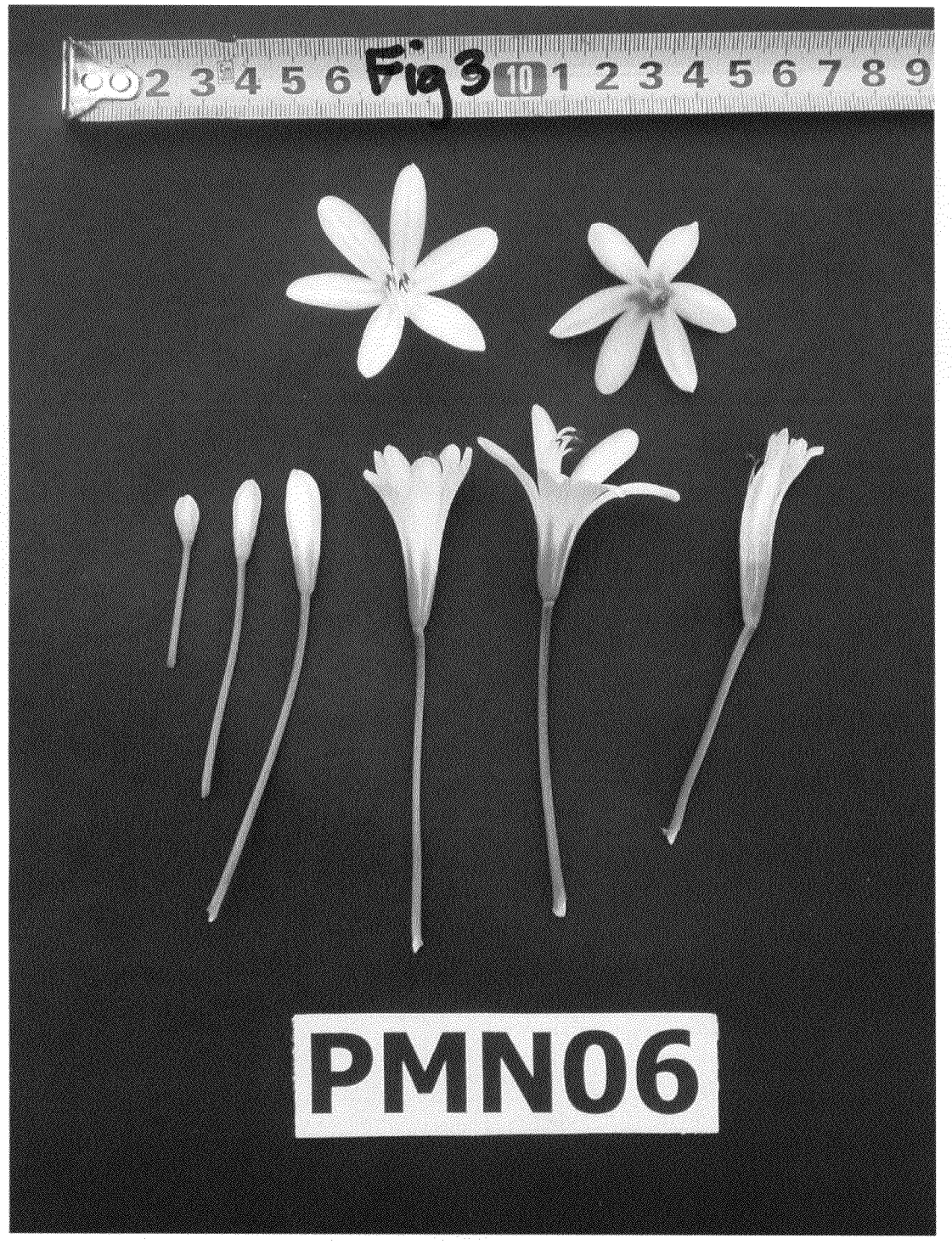
FIG. 3 show colors of 'PMN06' flowers as they develop.
Figure 4:
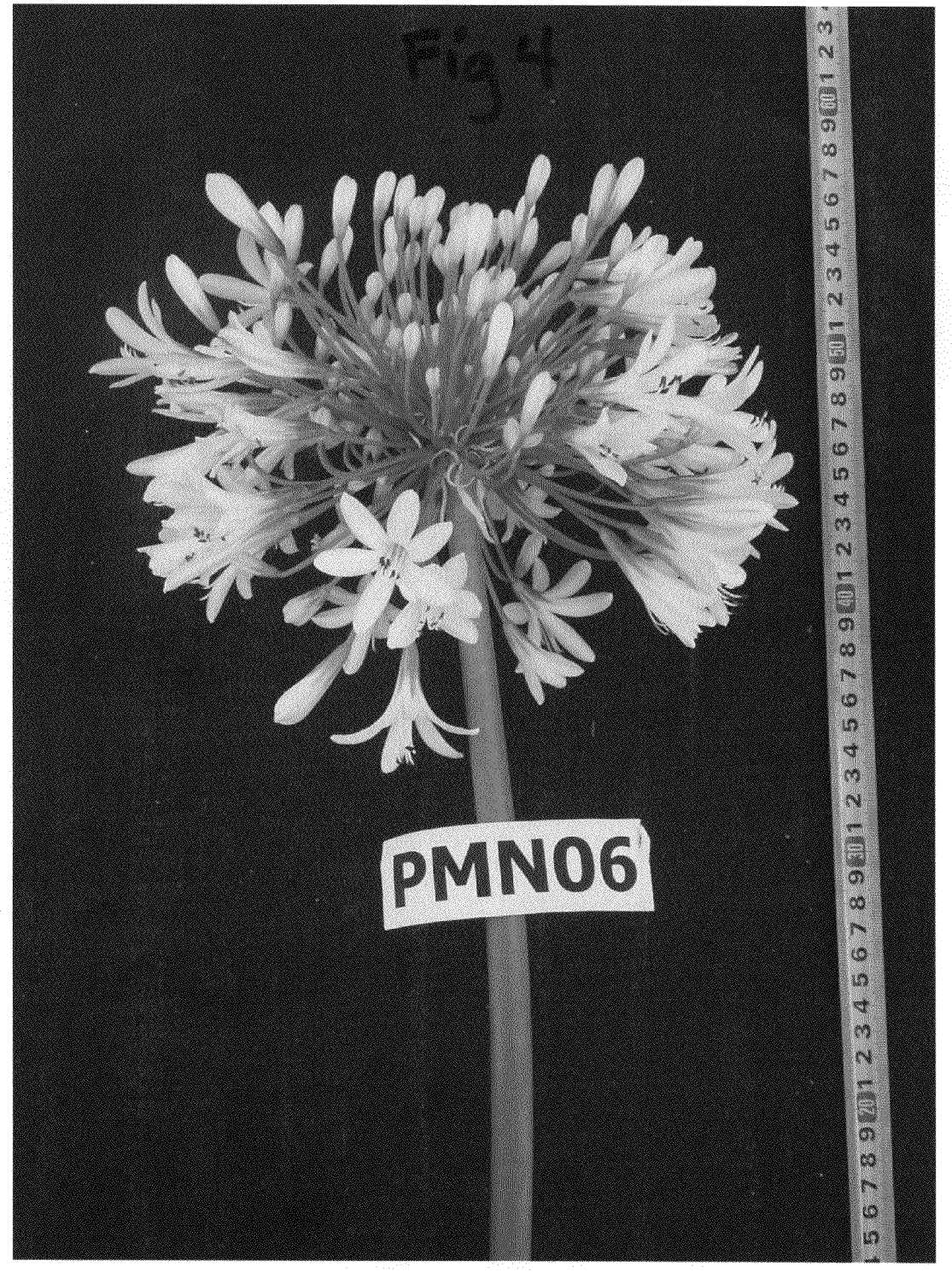
FIG. 4 shows an inflorescence of 'PMN06'.
Figure 5:
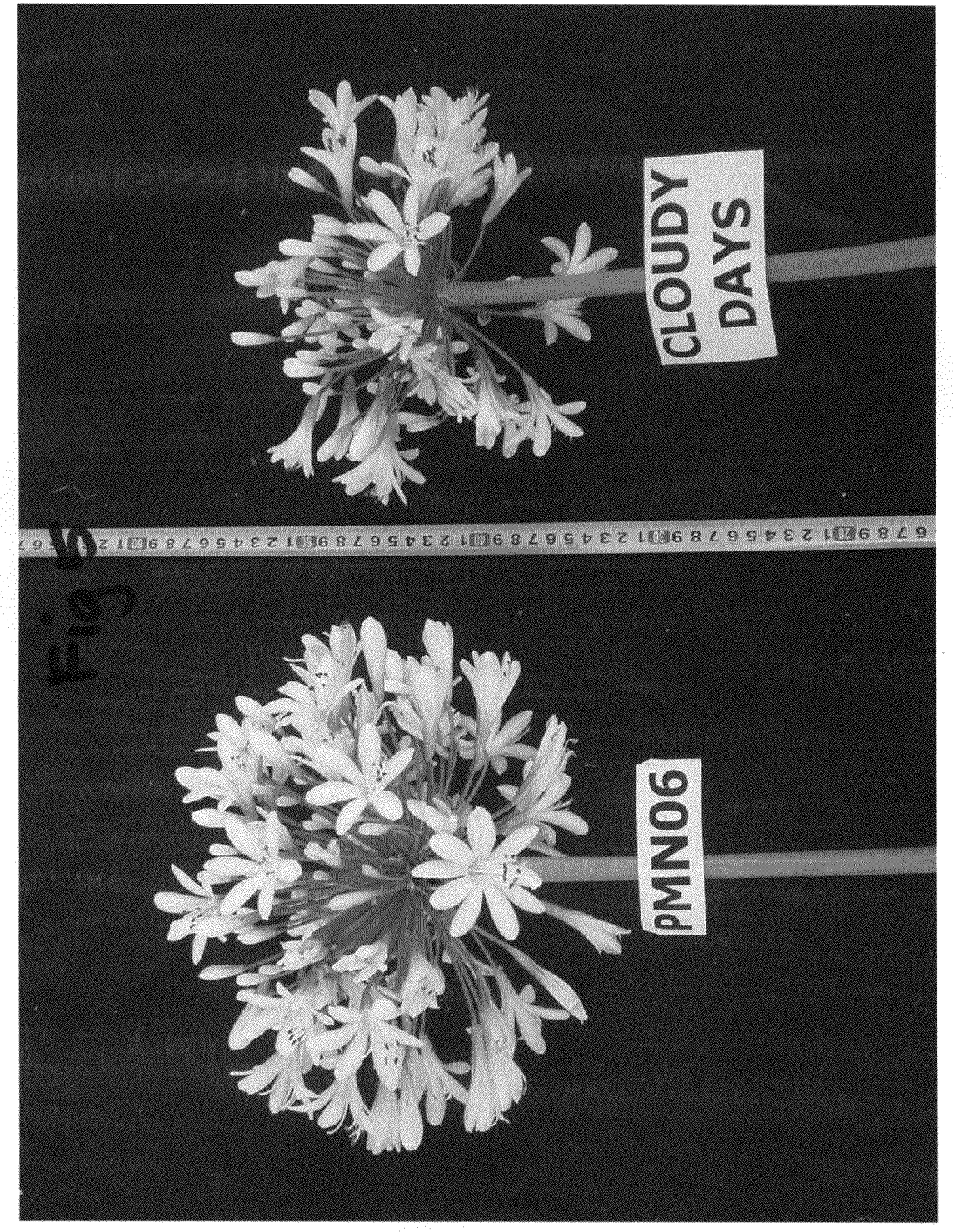
FIG. 5 shows a comparison between inflorescences of 'PMN06' (on left) and the similar variety 'Cloudy Days'.

The following is a detailed botanical description of a new and distinct variety of *Agapanthus orientalis* known as 'PMN06' based upon observations of 12-month old plants (propagated from division) grown in nursery pots in full sun in open beds in Pine Mountain, Queensland, Australia during early summer 2005 (as described below in connection with Table 1). Plant observations and descriptions were taken in early summer 2005.

Those skilled in the art will appreciate that certain characteristics will vary with older or, conversely, with younger plants. 'PMN06' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1995 edition.

'PMN06' is an evergreen perennial *Agapanthus orientalis*. 'PMN06' has violet-blue and white bicolored flowers on stems up to 90 cm high that develop in spring and early summer. These are expressed as a white inner perianth tube color and perianth lobes in contrast to a violet blue outer perianth tube color.

These characteristics are unusual for *Agapanthus orientalis*, as these plants usually have either solely a violet-blue flower form or solely a white flower form, without the contrast in color between the inner and outer perianth tube or the contrast between the outer perianth tube and the perianth lobes. A botanical description of 'PMN06' and comparisons with the common white and common violet blue forms of *Agapanthus orientalis* and the similar variety 'Cloudy Days' (unpatented) are provided below.

Technical Description of the Variety

Plant characteristics: Growth habit clumps of strap-like leaves from thick rhizomes, height of foliage medium (mean 53 cm), height including inflorescence 105 cm, flowering season late (commences late spring to early summer in south-east Queensland, Australia).

Leaves: Attitude erect to semi-erect, length medium (mean 44 cm), width medium (mean 42 mm), variegation absent, upper and lower side color yellow green (RHS 146A) shape ligulate, apex obtuse to broad acute, margin entire.

Inflorescence: Structure is umbellate, diameter medium (mean 23 cm), number of flowers medium (mean 144 per umbel), peduncle length medium (mean 86 cm), peduncle width medium (mean 14 mm), peduncle color yellow green (RHS 144A).

Flower: Type single, color of bud violet blue (RHS 93C-D), diameter medium (mean 44 mm), length medium (mean 42 mm), color of outer perianth tube violet blue (RHS 93C-D), color of inner perianth tube white (RHS 155D), perianth lobe length medium (mean 29 mm), perianth lobe width medium (mean 9.5 mm), pedicel length medium (mean 64 mm), pedicel diameter medium (mean 1.7 mm), pedicel color yellow green (RHS 144B) maturing distally to grayed green (approximately RHS 197A), color of new anthers gray (RHS 201A), color of pollen yellow green (RHS 153A), color of filaments, style and stigma white (approximately RHS155D).

Cold and heat tolerance: 'PMN06' has not yet been observed under all conditions. It is expected to exhibit cold tolerance typical of the species. Further testing for cold tolerance is ongoing. 'PMN06' is also very heat tolerant. It adapted well to the high heat and humidity conditions during summer in Pine Mountain, Queensland, Australia without any disease or insect damage.

Drought tolerance: 'PMN06' has not yet been observed under all conditions. It is expected to exhibit good drought tolerance typical of the species.

Pest resistance: No known pests.

Cultural conditions: 'PMN06' can tolerate a wide range of soil conditions.

Comparisons with Other *Agapanthus*

The parent form, *Agapanthus orientalis* 'PMN01', is characterized by a tall plant height, wide leaf width, erect leaf attitude, and weak violet blue and white bicolored flowers. 'PMN06' has a medium foliar height (53 cm on average) whereas 'PMN01' has a tall plant height (64 cm on average). 'PMN06' has leaves that measure 42 mm wide whereas the leaves of 'PMN01' measure 53 mm wide, on average. 'PMN06' exhibits a more arched habit with foliage that is semi erect to erect whereas the habit of 'PMN01' exhibits an erect habit. The violet color of the outer perianth of 'PMN06' is a deeper hue of violet blue (RHS 93C to RHS 93D) whereas the outer perianth of 'PMN01' has a weaker violet blue color (RHS 92C).

Comparisons with Other *Agapanthus*

'PMN06' is an attractive ornamental clump forming strappy leafed plant as compared with other *Agapanthus orientalis*. 'PMN06' is characterized by its distinctive violet-blue and white bicolored flowers borne on stems up to 90 cm high typically developing in late spring and early summer. 'PMN06' has violet-blue and white bicolored flowers, whereas the standard forms of *Agapanthus orientalis* have either solely violet-blue colored flowers or solely white colored flowers only (see Table 1).

*Agapanthus orientalis* 'Cloudy Days' (unpatented, Australian Plant Breeders Rights application no. 2001/354) is the most similar comparator variety to 'PMN06'. In comparison with *Agapanthus orientalis* 'Cloudy Days', cultivar 'PMN06' has a darker violet blue outer perianth tube color, a taller plant height including the inflorescence, a longer peduncle length, a greater number of flowers per inflorescence and a longer flower length (see Table 1).

A comparative trial of *Agapanthus* cultivar 'PMN06' with *Agapanthus orientalis* 'Cloudy Days' was carried out in early summer 2005 in Pine Mountain, Queensland, Australia. The data are presented in Table 1 below with additional comparison to the common white and common violet blue forms of *Agapanthus orientalis* collected in early summer 2000. The plants for this trial were propagated from divisions, planted into 200 mm pots filled with soilless potting mix, and grown in full sun for nine months before the trial started. Nutrition was maintained with slow release fertilizers; pest and disease treatments were not necessary. The trial was designed such that fifteen plants of each variety were arranged in a completely randomized manner. Measurements were taken from ten plants at random with one sample per plant.

TABLE 1

| Characteristic | *Agapanthus* Varieties | | | |
|---|---|---|---|---|
| | 'PMN06' | 'Cloudy Days' | *A. orientalis* (white form) | *A. orientalis* (violet blue form) |
| Plant Height (including inflorescence) | 105 cm | 88 cm | 110 cm | 112 cm |
| Plant Height (foliar only) | 53 cm | 44 cm | 44 cm | 52 cm |
| Peduncle length | 86 cm | 64 cm | 82 cm | 95 cm |
| Inflorescence diameter | 23 cm | 23 cm | 23 cm | 22 cm |
| Number of flowers per inflorescence | 144 | 86 | 130 | 130 |
| Leaf length | 44 cm | 38 cm | 38 cm | 48 cm |
| Leaf width | 42 mm | 39 mm | 38 mm | 41 mm |
| Flower diameter | 44 mm | 44 mm | 46 mm | 48 mm |
| Flower length | 42 mm | 37 mm | 42 mm | 45 mm |
| Perianth lobe length | 29 mm | 29 mm | 32 mm | 32 mm |

TABLE 1-continued

| Characteristic | *Agapanthus* Varieties | | | |
|---|---|---|---|---|
| | 'PMN06' | 'Cloudy Days' | *A. orientalis* (white form) | *A. orientalis* (violet blue form) |
| Flower bud color (RHS) | 93C-D | 93C-94C | 155D | 94B |
| Contrast between outer perianth tube color and perianth lobe color | present | present | absent | absent |
| Outer perianth tube color (RHS) | 93C-D | 93C-94C | 155D | 94C-D |
| Inner perianth lobe color (RHS) | 155D | 155D | 155D | 94C-D with stripe of 94B |

That which is claimed is:

1. A new and distinct variety of *Agapanthus orientalis* plant named 'PMN06', substantially as described and illustrated herein.

* * * * *

PMN06

PMN06

PMN06